United States Patent
Horellou et al.

(10) Patent No.: US 6,245,330 B1
(45) Date of Patent: Jun. 12, 2001

(54) RECOMBINANT ADENOVIRUSES CODING FOR GLIAL-DERIVED NEUROTROPHIC FACTOR (GDNF)

(75) Inventors: Philippe Horellou; Jacques Mallet, both of Paris; Michel Perricaudet, Ecrosnes; Frédéric Revah, Paris; Emmanuelle Vigne, Ivry Sur Seine, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 08/716,326

(22) PCT Filed: Mar. 23, 1995

(86) PCT No.: PCT/FR95/00356

§ 371 Date: Oct. 3, 1996

§ 102(e) Date: Oct. 3, 1996

(87) PCT Pub. No.: WO95/26408

PCT Pub. Date: Oct. 5, 1995

(30) Foreign Application Priority Data

Mar. 25, 1994 (FR) .................................................. 94 03542

(51) Int. Cl.[7] .......................... A61K 48/00; C12N 15/00; C12N 15/88
(52) U.S. Cl. ........................ 424/93.2; 514/44; 435/320.1; 435/455
(58) Field of Search .......................... 514/44; 435/320.1, 435/325; 424/93.1, 93.21, 93.2

(56) References Cited

U.S. PATENT DOCUMENTS 5,670,488 * 9/1997 Gregory et al. ........................ 514/44

FOREIGN PATENT DOCUMENTS

| 2 688 514 | 3/1992 | (FR) . |
| WO 94/08026 | 9/1993 | (WO) . |
| WO 94/20146 | 2/1994 | (WO) . |

OTHER PUBLICATIONS

Thimmappaya et al. Adenovirus VAI RNA is Required for Efficient Translation of Viral mRNAs at Late Times after Infection. Cell, vol. 31, pp. 543–551, 1982.*

Reynolds et al. Central nervous system growth and differentiation factors: clinical horizons—truth or dare? Current Opinion in Biotechnology, vol. 4, No. 6, pp. 734–738, Dec. 1993.*

Strafford–Perricaudet et al. Widespread long–term gene transfer to mouse skeletal muscles and heart. J. Clin. Invest., vol. 90, pp. 626–630, Aug. 1992.*

Breakefield, X. O. Gene delivery into the brain using virus vectors. Nature Genetics, vol. 3, pp. 187–189. Mar. 1993.*

Orkin et al. Report and recommendations of the panel to assess the NIH investment in research on gene therapy. Issued by the NIH, Dec. 7, 1995.*

Congress of the French Society of Hematology, vol. 35, No. 3, 299–300, (1993), Peschanski Lisovoski Akli Caillaud Wahrman, Gene Transfer for Therapeutic Purposes in the Central Nervous System.

NeuroReport, 5, 7, 801–804, (1994) Ridoux Robert Zhang Perricaudet Mallet Le Gal La Salle, The use of adenovirus vectors for intracerebral grafting of transfected nervous cells.

Molecular Biology of the Cell, 4, 442A, (1993) Baetge Emerich Winn Lee Lindner Hammang, Delivery of a Putative Parkinson's Factor (GDNF) Into the Rat CNS Using a Polymer–Encapsulated Cell Line.

European Journal of Biochemistry, 208, 2, 211–225, (1992) Roemer Friedman, Concepts and Strategies for Human Gene Therapy.

Brain Research, 648, 1, 171–175, (1994) Ridoux Robert Zhang Perricaudet Mallet Le Gal La Salle, Adenoviral Vectors as Functional Retrograde Neuronal Tracers.

Medicine/Sciences, 9, 2, 208–210, (1993) Danos Moullier Heard, Reimplantation de cellules genetiquement modifiees dans des neo–organes vascularises.

Science, 256, 5063, 1550–152, (1992) Culver Ram Wallbridge Ishii Oldfield Blaese. In Vivo Gene Transfer with Retroviral Vector–Producer Cells for Treatment of Experimental Brain Tumors.

Science, 259, 988–990, (1993) Le Gal La Salle Berrard Ridoux Stratford–Perricaux Perricaudet Mallet, An Adenovirus Vector for Gene Transfer into Neurons and Glia in the Brain.

* cited by examiner

*Primary Examiner*—Dave Trong Nguyen
(74) *Attorney, Agent, or Firm*—Finnegan, Henderson, Farabow, Garrett & Dunner L.L.P.

(57) ABSTRACT

Recombinant adenoviruses comprising a heterologous DNA sequence coding for glial-derived neurotrophic growth factor (GDNF) are provided. The recombinant adenoviruses are useful in a method of expressing GDNF in a cell, wherein the cell is present in a mammal suffering from Parkinson's disease, comprising infecting said cell with a replication-defective recombinant adenovirus comprising a DNA sequence encoding GDNF operably linked to a promoter by administering the adenovirus into cells of the central nervous system. The recombinant adenoviruses of the invention are also useful in a method of treating Parkinson's disease comprising administering into cells of the central nervous system of a mammal suffering therefrom a replication defective recombinant adenovirus comprising ITRs, an encapsidation sequence and a DNA sequence encoding GDNF operably linked to a promoter, wherein the adenovirus E1 gene is non-functional and GDNF is expressed at a level that provides a therapeutic effect.

24 Claims, 1 Drawing Sheet

RECOMBINANT ADENOVIRUSES CODING FOR GLIAL-DERIVED NEUROTROPHIC FACTOR (GDNF)

This application is a 371 of PCT/FR95/00356, filed Mar. 23, 1995.

The present invention relates to recombinant adenoviruses which contain a DNA sequence encoding the glial cell-derived neurotrophic factor. The invention also relates to the preparation of these vectors, to the pharmaceutical compositions which contain them, and to their therapeutic use, especially in gene therapy, for treating and/or preventing neurodegenerative diseases.

The increase in the length of life in Western countries is accompanied by a steady growth in neurode-generative diseases such as Alzheimer's disease, Parkinson's disease, Huntington's chorea, amyotrophic lateral sclerosis, etc. Thus, Parkinson's disease, for example, affects 4% of people above the age of 65, and Alzheimer's disease affects 10% of those above the age of 70 and 30% of those above the age of 80. Generally speaking, all these diseases result from a progressive loss of neuronal cells in the central nervous system, or even within very localized structures, as in the case of Parkinson's disease.

During recent years, numerous research programmes have been developed in order to understand the mechanisms of this degeneration associated with ageing, with a view to developing means for treating it, and also for preventing it, by gene therapy.

Since the neurodegenerative diseases are an expression of the progressive death of the neuronal cells, stimulation of the production of the growth factors involved in the development of these neuronal cells has in fact appeared to be a possible route for preventing and/or opposing this degeneration.

The object of the present invention is, in particular, to propose vectors which make it possible directly to promote the survival of the neuronal cells which are involved in these pathologies by means of expressing, in an efficient and localized manner, certain trophic factors.

The trophic factors are a class of molecules which possess properties of stimulating axonal growth or the survival of the nerve cells. The first factor possessing neurotrophic properties, NGF ("Nerve Growth Factor"), was characterized some 40 years ago (for review, see Levi-Montalcini and Angelleti, Physiol. Rev. 48 (1968) 534). Other neurotrophic factors, in particular the glial cell-derived neurotrophic factor (GDNF) (L.-F. Lin, D. Doherty, J. Lile, S. Besktesh, F. Collins, Science, 260, 1130–1132 (1993)) have only been identified recently. GDNF is a protein of 134 amino acids with a molecular weight of 16 kD. Its essential function is the in-vitro promotion of the survival of dopaminergic neurones.

The present invention is particularly advantageous for administering GDNF in the form of a therapeutic agent.

More precisely, the present invention is directed towards developing vectors which are particularly effective in delivering, in vivo and in a localized manner, therapeutically active quantities of the specific gene encoding GDNF in the nervous system.

In application No. PCT/EP93/02519, which is pending concomitantly, it was demonstrated that it was possible to use the adenoviruses as vectors for transferring a foreign gene in vivo into the nervous system and expressing the corresponding protein.

More specifically, the present invention relates to specially adapted and efficient novel constructs for transferring glial cell-derived neurotrophic factor (GDNF).

More precisely, it relates to a recombinant adenovirus which encompasses a DNA sequence encoding GDNF or one of its derivatives, to its preparation, and to its use for treating and/or preventing neurodegenerative diseases.

Thus, the Applicant has clearly demonstrated that it is possible to construct recombinant adenoviruses which contain a sequence encoding GDNF, and to administer these recombinant adenoviruses in vivo, and that this administration permits stable and localized expression of therapeutically active quantities of GDNF in vivo, in particular in the nervous system and without any cytopathic effect.

An initial subject of the invention is thus a defective recombinant adenovirus which encompasses at least one DNA sequence encoding all, or an active part, of the glial cell-derived neurotrophic factor (GDNF) or one of its derivatives.

The glial cell-derived neurotrophic factor (GDNF) which is produced within the scope of the present invention can either be human GDNF or an animal GDNF.

The cDNA sequences encoding human GDNF and rat GDNF have been cloned and sequenced (L.-F. Lin, D. Doherty, J. Lile, S. Besktesh, F. Collins, Science, 260, 1130–1132 (1993)).

The DNA sequence which encodes GDNF and which is used within the scope of the present invention can be a cDNA, a genomic DNA (gDNA), or a hybrid construct consisting, for example, of a cDNA in which one or more introns could be inserted. The sequence may also consist of synthetic or semisynthetic sequences. Particularly advantageously, the sequence of the present invention encodes GDNF which is preceded by the native pro region (pro GDNF).

Particularly advantageously, a cDNA or a gDNA is employed. According to a preferred embodiment of the invention, the sequence is a gDNA sequence encoding GDNF. Use of this latter sequence can make it possible to achieve improved expression in human cells.

Naturally, prior to its incorporation into an adenovirus vector according to the invention, the DNA sequence is advantageously modified, for example by site-directed mutagenesis, especially in order to insert appropriate restriction sites. Thus, the sequences described in the prior art are not constructed so that they can be used in accordance with the invention, and preliminary adaptations may prove to be necessary in order to obtain a substantial level of expression.

Within the meaning of the present invention, a derivative of GDNF is understood to mean any sequence which is obtained by modification and which encodes a product which retains at least one of the biological properties of GDNF (trophic effect and/or differentiating effect). Modification should be understood to mean any mutation, substitution, deletion, addition or modification of a genetic and/or chemical nature. These modifications can be effected by techniques known to the person skilled in the art (see general molecular biological techniques below). The derivatives within the meaning of the invention can also be obtained by hybridization from nucleic acid libraries, using the native sequence or a fragment thereof as the probe.

These derivatives are, in particular, molecules which have a greater affinity for their sites of attachment, sequences which permit improved expression in vivo, molecules which are more resistant to proteases, and molecules which have greater therapeutic efficacy or less pronounced secondary effects, or, perhaps, novel biological properties.

The preferred derivatives which may most particularly be cited are natural variants, molecules in which one or more residues have been replaced, derivatives which have been obtained by deleting regions which are not involved, or only involved to a limited extent, in the interaction with the binding sites under consideration, or which express an undesirable activity, and derivatives which include residues which are additional to those in the native sequence, such as, for example, a secretory signal and/or a junction peptide.

According to one preferred embodiment of the invention, the DNA sequence encoding GDNF or one of its derivatives also includes a secretory signal which makes it possible to direct the synthesized GDNF into the secretory paths of the infected cells. According to one preferred embodiment, the DNA sequence contains a secretory sequence in the 5' position and in reading frame with the sequence encoding the GDNF. In this way, the synthesized GDNF is advantageously released into the extracellular compartments and can in this way activate its receptors. The secretory signal is advantageously the native secretory signal of the GDNF (referred to below by the term "pre"). However, the secretory signal can also be a secretory signal which is heterologous or even artificial. Advantageously, the DNA sequence encodes pre-GDNF or, more particularly, human pre-GDNF.

Advantageously, the sequence encoding GDNF is placed under the control of signals which allow the GDNF to be expressed in nerve cells. Preferably, these signals are heterologous expression signals, that is signals which are different from those which are naturally responsible for expressing GDNF. They may, in particular, be sequences which are responsible for expressing other proteins, or synthetic sequences. In particular, they can be promoter sequences from eucaryotic or viral genes. For example, they can be promoter sequences derived from the genome of the cell which it is wished to infect. Similarly, they can be promoter sequences derived from the genome of a virus, including the adenovirus being used. Examples of promoters which may be cited in this regard are E1A, MLP, CNV, RSV LTR, etc. Furthermore, these expression sequences can be modified by adding activation sequences or regulatory sequences, or sequences which allow tissue-specific expression. Thus, it can be of particular interest to use expression signals which are active specifically, or in the main, in nerve cells, such that the DNA sequence is only expressed, and only produces its effect, when the virus has actually infected a nerve cell. Examples of promoters which may be cited in this respect are those of the neurone-specific enolase, of GFAP, etc.

In a first specific embodiment, the invention relates to a defective recombinant adenovirus which includes a cDNA sequence encoding human pre-GDNF under the control of the RSV LTR promoter.

In a second specific embodiment, the invention relates to a defective recombinant adenovirus which includes a gDNA sequence encoding human pre-GDNF under the control of the RSV LTR promoter.

Thus, the Applicant has demonstrated that the LTR promoter of the Rous sarcoma virus (RSV) enabled GDNF to be expressed over a long period and at a substantial level in the cells of the nervous system, in particular of the central nervous system.

Still within a preferred embodiment, the invention relates to a defective recombinant adenovirus which includes a DNA sequence encoding the whole, or an active part, of human GDNF, or of a derivative thereof, under the control of a promoter which enables most expression to take place in the nervous system.

A particularly preferred embodiment of the present invention is a defective recombinant adenovirus which includes the ITR sequences, a sequence allowing encapsidation, and a DNA sequence encoding glial cell-derived human neurotrophic factor (hGDNF), or a derivative thereof, under the control of a promoter allowing most of the expression to take place in the nervous system, and in which the E1 gene, and at least one of the genes E2, E4 and L1–L5 is non-functional.

Defective adenoviruses according to the invention are adenoviruses which are incapable of replicating autonomously in the target cell. In general, the genome of the defective adenoviruses used within the scope of the present invention therefore lacks at least those sequences which are necessary for the said virus to replicate in the infected cell. These regions may be removed (in whole or in part), or rendered non-functional, or replaced by different sequences, in particular by the DNA sequence encoding GDNF.

The defective virus of the invention preferably retains those sequences of its genome which are necessary for encapsidating the viral particles. Still more preferably, as indicated above, the genome of the defective recombinant virus according to the invention includes the ITR sequences, a sequence allowing encapsidation, the non-functional E1 gene, and a non-functional version of at least one of the genes E2, E4 and L1–L5.

Different serotypes of adenovirus exist, whose structures and properties vary to some degree. Of these serotypes, preference is given to using the type 2 or type 5 human adenoviruses (Ad 2 or Ad 5) or the adenoviruses of animal origin (see application FR 93 05954) within the scope of the present invention. Adenoviruses of animal origin which can be used within the scope of the present invention and which may be mentioned are the adenoviruses of canine, bovine, murine (example: Mav1, Beard et al., Virology 75 (1990) 81), ovine, porcine, avian and also simian (example: SAV) origin. The adenovirus of animal origin is preferably a canine adenovirus, more preferably a CAV2 adenovirus [Manhattan strain or A26/61 (ATCC VR-800) for example]. Adenoviruses of human or canine origin, or a mixture of these, are preferably employed within the scope of the invention.

The defective recombinant adenoviruses according to the invention can be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence encoding GDNF. The homologous recombination takes place after cotransfection of the said adenovirus and plasmid into an appropriate cell line. The cell line which is employed should preferably (i) be transformable by the said elements, and (ii) contain the sequences which are able to complement the defective adenovirus genome part, preferably in an integrated form in order to avoid the risk of recombination. As an example of a cell line, mention may be made of the human embryonic kidney cell line 293 (Graham et al., J. Gen. Virol. 36 (1977) 59) which contains, in particular, integrated into its genome, the left-hand part of the genome of an Ad5 adenovirus (12%). Strategies for constructing vectors derived from adenoviruses have also been described in applications Nos. FR 93 05954 and FR 93 08596, which are incorporated herein by reference.

Afterwards, the adenoviruses which have multiplied are recovered and purified using conventional molecular biological techniques, as illustrated in the examples.

The properties of the vectors of the invention which are particularly advantageous ensue, in particular, from the construct employed (defective adenovirus, in which certain viral regions are deleted), from the promoter which is employed for expressing the sequence encoding GDNF (preferably a viral or tissue-specific promoter), and from the methods of administering the said vector, resulting in an expression of GDNF which is efficient and which takes place in the appropriate tissues. The present invention thus provides viral vectors which can be employed directly in gene therapy, and which are particularly suitable and efficient for directing expression of GDNF in vivo. The present invention thus offers a novel approach which is particularly advantageous for treating and/or preventing neurodegenerative diseases.

The present invention also relates to any employment of an adenovirus such as described above for preparing a pharmaceutical composition which is intended for treating and/or preventing neurodegenerative diseases.

More especially, it relates to any employment of these adenoviruses for preparing a pharmaceutical composition which is intended for treating and/or preventing Parkinson's disease, Alzheimer's disease, amyotrophic lateral sclerosis (ALS), Huntington's disease, epilepsy and vascular dementia.

The present invention also relates to a pharmaceutical composition which includes one or more defective recombinant adenoviruses such as those previously described. These pharmaceutical compositions can be formulated with a view to administering them by the topical, oral, parenteral, intranasal, intravenous, intramuscular, subcutaneous, intraocular or transdermal, route, inter alia. Preferably, the pharmaceutical compositions of the invention contain an excipient which is pharmaceutically acceptable for an injectable formulation, in particular for injection directly into the nervous system of the patient. These injectable formulations can, in particular, be sterile, isotonic solutions, or dry, in particular lyophilized, compositions which, by means of sterile water or physiological saline, as the case may be, being added to them, enable injectable solutions to be constituted. Direct injection into the nervous system of the patient is advantageous since it enables the therapeutic effect to be concentrated at the level of the affected tissues. Direct injection into the central nervous system of the patient is advantageously effected using a stereotactic injection apparatus. The reason for this is that use of such an apparatus renders it possible to target the injection site with a high degree of precision.

In this respect, the invention also relates to a method for treating neurodegenerative diseases which comprises administering a recombinant adenovirus such as defined above to a patient. More especially, the invention relates to a method for treating neurodegenerative diseases which comprises stereotactically administering a recombinant adenovirus such as defined above.

The doses of defective recombinant adenovirus which are employed for the injection can be adjusted depending on different parameters, in particular depending on the mode of administration employed, on the pathology concerned, and also on the sought-after duration of the treatment. Generally, the recombinant adenoviruses according to the invention are formulated and administered in the form of doses consisting of between $10^4$ and $10^{14}$ pfu/ml, preferably from $10^6$ to $10^{10}$ pfu/ml. The term pfu ("plaque-forming unit") represents the infective power of a virus solution, and is determined by infecting an appropriate cell culture and then measuring, in general after 48 hours, the number of plaques of infected cells. The techniques for determining the pfu titre of a viral solution are well documented in the literature.

The invention also relates to any mammalian cell which is infected with one or more defective recombinant adenoviruses such as described above. More especially, the invention relates to any population of human cells which is infected with these adenoviruses. These cells can, in particular, be fibroblasts, myoblasts, hepatocytes, keratinocytes, endothelial cells, glial cells, etc.

The cells according to the invention can be derived from primary cultures. These cells can be removed by any technique known to the person skilled in the art and then cultured under conditions which allow them to proliferate. As regards fibroblasts, more especially, these cells can readily be obtained from biopsies, for example using the technique described by Ham [Methods Cell. Biol. 21a (1980) 255]. These cells can be employed directly for infection with the adenoviruses, or be preserved, for example by freezing, in order to establish autologous banks for subsequent use. These cells according to the invention can also be secondary cultures which are obtained, for example, from pre-established banks.

The cells in culture are then infected with recombinant adenoviruses in order to confer on the cells the capacity to produce GDNF. The infection is carried out in vitro using techniques known to the person skilled in the art. In particular, the person skilled in the art can adjust the multiplicity of infection and, where appropriate, the number of cycles of infection which is carried out, in accordance with the type of cells employed and with the number of virus copies per cell which is required. Naturally, these steps have to be performed under appropriate conditions of sterility since the cells are destined for in-vivo administration. The doses of recombinant adenovirus which are employed for infecting the cells can be adjusted by the person skilled in the art in accordance with the sought-after objective. The conditions described above for administration in vivo can be applied to infection in vitro.

The invention also relates to an implant comprising mammalian cells which are infected with one or more defective recombinant adenoviruses as described above, and an extracellular matrix. Preferably, the implants according to the invention comprise from $10^5$ to $10^{10}$ cells. More preferably, they comprise from $10^6$ to $10^8$ cells.

More especially, the extracellular matrix in the implants of the invention comprises a gel-forming compound and, where appropriate, a support for anchoring the cells.

Different types of gel-forming agents can be employed for preparing implants according to the invention. The gel-forming agents are used in order to enclose the cells in a matrix having a gel constitution, and, if the need arises, in order to facilitate anchorage of the cells on the support. Various cell adhesion agents can, therefore, be used as gel-forming agents, such as, in particular, collagen, gelatin, glycosaminoglycans, fibronectin, lectins, etc. Collagen is preferably used within the scope of the present invention. This collagen can be of human, bovine or murine origin. More preferably, type I collagen is used.

As indicated above, the compositions according to the invention advantageously comprise a support for anchoring the cells. The term anchoring denotes any form of biological and/or chemical and/or physical interaction leading to adhesion and/or attachment of the cells to the support. Moreover, the cells can cover the support which is used and/or penetrate into the interior of this support. Within the scope of the invention, preference is given to using a non-toxic and/or biocompatible solid support. In particular, use may be made of polytetrafluoroethylene (PTFE) fibres or of a support of biological origin.

The implants according to the invention can be implanted at different sites in the organism. In particular, implantation can be effected at the level of the peritoneal cavity, in subcutaneous tissue (suprapubic region, iliac or inguinal fossae, etc.), in an organ, a muscle, a tumour, the central nervous system, and also under a cornification. The implants according to the invention are particularly advantageous in that they make it possible to control the release of the therapeutic product within the organism: this release is initially determined by the multiplicity of infection and by the number of implanted cells. After that, the release can be controlled by the shrinkage of the implant, which definitively stops the treatment, or by using regulatable expression systems which enable expression of the therapeutic genes to be induced or repressed.

The present invention thus offers a very efficient means for treating and/or preventing neurodegenerative diseases. It is quite particularly adapted for treating Alzheimer's, Parkinson's and Huntington's diseases, and for treating ALS. Furthermore, the adenoviral vectors according to the invention display important advantages which are linked, in particular, to their very high efficiency in infecting nerve cells, thereby making it possible to achieve infections using low volumes of viral suspension. In addition, infection with the adenoviruses of the invention is localized to a high degree to the site of injection thereby avoiding the risk of any diffusion into adjacent cerebral structures.

Furthermore, this treatment can be used just as easily for humans as for any animal such as sheep, cattle, domestic animals (dogs, cats, etc.), horses, fish, etc.

The present invention will be described in more detail using the following examples, which must be regarded as illustrating the invention and not limiting

GENERAL MOLECULAR BIOLOGICAL TECHNIQUES

Figure 1:
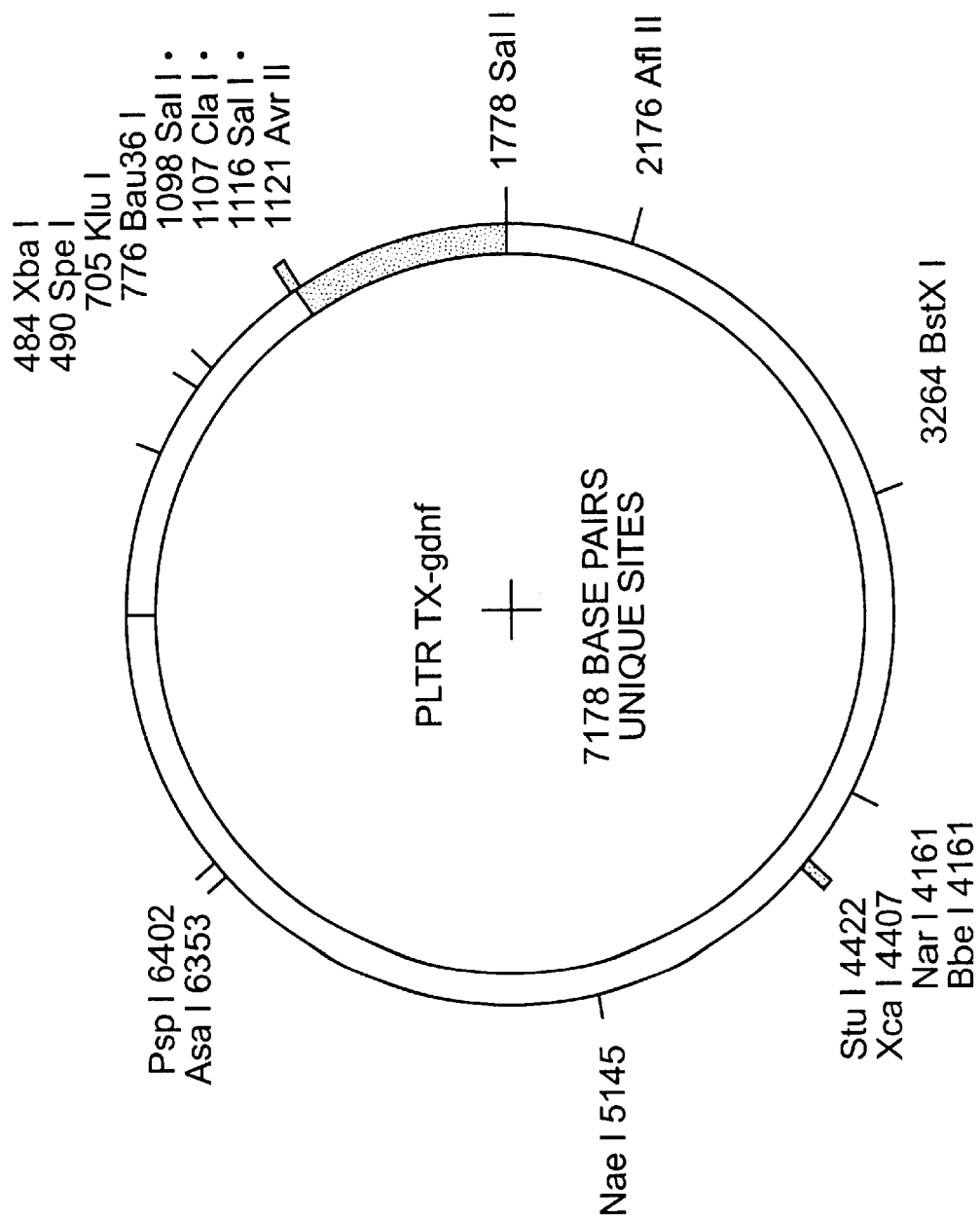
FIG. 1: Depiction of the vector pLTR IX-GDNF

The standard methods employed in molecular biology such as preparative extractions of plasmid DNA, centrifugation of plasmid DNA in a caesium chloride gradient, electrophoresis on agarose or acrylamide gels, purification of DNA fragments by electroelution, extraction of proteins with phenol or with phenol/chloroform, precipitation of DNA in a saline medium using ethanol or isopropanol, transformation into Escherichia coli, etc., are well known to the person skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The plasmids such as pBR322 and pUC, and the phages of the M13 series were obtained commercially (Bethesda Research Laboratories).

For the ligations, the DNA fragments can be separated according to their size by electrophoresis in agarose or acrylamide gels, extracted with phenol or with a phenol/chloroform mixture, precipitated by thanol and then incubated in the presence of T4 phage NA ligase (Biolabs) in accordance with the supplier's instructions.

The protruding 5' ends can be filled in using the Klenow fragment of E. coli DNA polymerase I (Biolabs) in accordance with the supplier's specifications. The protruding 3' ends are destroyed in the presence of T4 phage DNA polymerase (Biolabs), which is employed in accordance with the manufacturer's instructions. The protruding 5' ends are destroyed by careful treatment with SI nuclease.

In vitro site-directed mutagenesis using synthetic oligodeoxynucleotides can be performed using the method developed by Taylor et al. [Nucleic Acids Res. 13 (1985) 8749–8764] and employing the kit distributed by Amersham.

Enzymic amplification of DNA fragments by the technique termed PCR [polymerase-catalysed chain reaction, Saiki R. K. et al., Science 230 (1985) 1350–1354; Mullis K. B. et Faloona F. A., Meth. Enzym. 155 (1987) 335–350] can be performed using a "DNA thermal cycler" (Perkin Elmer Cetus) in accordance with the manufacturer's specifications.

The nucleotide sequences can be verified by means of the method developed by Sanger et al. [Proc. Natl. Acad. Sci. USA, 74 (1977) 5463–5467] using the kit distributed by Amersham.

EXAMPLES

Example 1

Construction of the Vector pLTR IX-GDNF.

This example describes the construction of the vector pLTR IX-GDNF, which contains the sequence encoding rat pre-GDNF under the control of the RSV virus LTR, as well as adenovirus sequences which permit in-vivo recombination.

Cloning of a cDNA encoding rat pre-GDNF. The cloning is effected by means of the PCR technique, which makes use of rat glial cell cDNA which is obtained by reverse transcription of RNA derived from these cells, employing the following oligonucleotides as templates:

5' Oligonucleotide: CCGTCGACCTAGGCCACCAT-GAAGTTA TGGGATGTC SEQ ID NO: 1

3' Oligonucleotide: CCGTCGACATGCATGAGCTCA-GATACA TCCACACC SEQ ID NO: 2

After the fragments obtained by the PCR technique had been subjected to gel purification and cut with the restriction enzyme SalI, they were inserted into a Bluescript (Stratagene) plasmid in the SalI site. A polyadenylation sequence derived from SV40 had previously been introduced into the XhoI site of the same plasmid. This plasmid is termed SK-GDNF-PolyA.

The vector pLTRIX-GDNF was obtained by introducing an insert, obtained by cutting SK-GDNF-PolyA with ClaI and KpnI (KpnI ends rendered blunt), between the ClaI and EcoRV sites of the plasmid pLTRIX (Stratford,Perricaudet et al., J; Clin. Invest. 90(1992) p 626).

Example 2

Construction of Recombinant Adenoviruses containing a sequence encoding GDNF The vector pLTR IX-GDNF was linearized and cotransfected together with a defective adenoviral vector into helper cells (cell line 293) supplying the functions encoded by the adenovirus E1 (E1A and E1B) regions in trans.

More precisely, the adenovirus Ad-GDNw was obtained by means of in-vivo homologous recombination between the mutant adenovirus Ad-dl1324 (Thimmappaya et al., Cell 31 (1982) 543) and vector pLTR IX-GDNF, in accordance with the following protocol: plasmid pLTR IX-GDNF and adenovirus Ad-dl1324, linearized with the enzyme ClaI, were cotransfected into cell line 293 in the presence of calcium phosphate in order to enable homologous recombination to take place. The recombinant adenoviruses which were thereby generated were selected by plaque purification. Following isolation, the DNA of the recombinant adenovirus was amplified in cell line 293, resulting in a culture supernatent being obtained which contains non-purified defective recombinant adenovirus having a titre of approximately $10^{10}$ pfu/ml.

The virus particles are subsequently purified by gradient centrifugation.

Example 3
In-vivo Transfer of the GDNF Gene by Means of a Tecombinant Adenovirus Into Rats Having a Lesion in the Nigrostriatal Tract.

This example describes the in-vivo transfer of the GDNF gene using an adenoviral vector according to the invention. It demonstrates, using an animal model of the nigrostriatal tract lesion, that the vectors of the invention render it possible to induce expression of therapeutic quantities of GDNF in vivo.

The nigrostriatal tract of rats which had previously been anaesthetized was damaged at the level of the median mesencephalic tract (MFB) by injecting the toxin 6-hydroxydopamine (6OH-DA). This chemical lesion induced by injection was unilateral, in accordance with the following stereotactic coordinates: AP: 0 and −1; ML: +1.6; V: −8.6 and −9 (the AP and ML coordinates are determined in relation to the bregma, and the V coordinate in relation to the dura mater). The line of incision is fixed at the level +5 mm.

Immediately after the lesion had been made, the recombinant GDNF adenovirus was injected into the substantia nigra and the striatum on the side of the lesion. More especially, the adenovirus which is injected is the Ad-GDNF adenovirus, which was previously prepared and which was used in purified form ($3.5 \times 10^6$ pfu/µl) in a phosphate-buffered saline (PBS) solution.

The injections were carried out using a canula (280 µm external diameter) which was connected to a pump. The speed of injection is fixed at 0.5 µl/min, after which the canula remains in place for a further 4 minutes before being removed. The volumes injected into the striatum and the substantia nigra are 2×3 µl and 2 µl, respectively. The concentration of adenovirus which is injected is $3.5 \times 10^6$ pfu/µl.

The following stereotactic coordinates are used for injection into the substantia nigra: AP=−5.8; ML=+2; V=−7.5 (the AP and ML coordinates are determined in relation to the bregma and the V coordinate in relation to the dura mater).

The following stereotactic coordinates are used for the injections into the striatum: AP=+0.5 and −0.5; ML=3; V=−5.5 (the AP and ML coordinates are determined in relation to the bregma, and the V coordinate in relation to the dura mater).

The therapeutic effects of administering the adenovirus according to the invention were demonstrated by three types of analysis: histological and immunohistochemical analysis, quantitative analysis and behavioural analysis.

Histological and Immunohistochemical Analysis

The chemical lesion in the nigrostriatal tract induces neuronal loss in the substantia nigra as well as dopaminergic denervation in the striatum (changes which are revealed in immunohistology by means of using an anti-tyrosine hydroxylase, TH, antibody).

Histological analysis of the injected brains is carried out three weeks after injecting the Ad-GDNF adenovirus intracerebrally under the conditions described in Example 6. Serial coronal sections of 30 µm in thickness are taken from the substantia nigra and the striatum. Sections spaced at intervals of 180 µm (1 section in 6) are stained with cresyl violet (in order to assess neuronal density) and immunolabelled with an anti-tyrosine hydroxylase (TH) antibody (in order to detect the dopaminergic neurones in the substantia nigra and their innervation in the striatum).

Quantitative Analysis

The number of dopaminergic neurones (TH-positive) in the substantia nigra is the parameter for evaluating the effects of the Ad-GDNF adenovirus. Counting is carried out on a sample (1 section in 6 for the whole of the length of the substantia nigra). For each section, the TH-positive neurones are counted separately on the two sides of the substantia nigra. The accumulated results for all the sections are expressed in the ratio: number of TH-positive neurones on the damaged side in relation to the number of TH-positive neurones on the undamaged side.

Behavioural Analysis

In order to evaluate the protective functional effects engendered by an injection of Ad-GDNF adenovirus on the lesion in the nigrostriatal tract, the sensorimotor performances of the animals are analysed during 2 behavioural tests: The test of the rotation induced by dopaminergic agonists (apomorphine, amphetamine and laevodopa), and the prehension ("paw-reaching") test.

---

What is claimed is:

1. A method of expressing GDNF in a cell, wherein the cell is present in a mammal suffering from Parkinson's disease, comprising infecting said cell with a replication-defective recombinant adenovirus comprising a DNA sequence encoding GDNF operably linked to a promoter, by administering the adenovirus into cells of the central nervous system.

2. The method of claim 1, wherein the DNA sequence further comprises a secretory sequence in the 5' position and in reading frame with the sequence encoding the GDNF.

3. The method of claim 1, wherein the DNA sequence is a cDNA sequence.

4. The method of claim 1, wherein the DNA sequence encodes human GDNF.

5. The method of claim 1, wherein the DNA sequence encoding GDNF is operably linked to a second sequence enabling expression in nerve cells.

6. The method of claim 1, wherein the promoter is a viral promoter.

7. The method of claim 6, wherein the promoter is an E1A, MLP, CMV, or RSV LTR promoter.

8. The method of claim 1, wherein the DNA sequence is a cDNA sequence encoding human pre-GDNF and the promoter is an RSV LTR promoter.

9. The method of claim 1, wherein the promoter enables expression in nerve cells.

10. The method of claim 9, wherein the promoter is a neuron-specific enolase promoter or a GFAP promoter.

11. The method of claim 1, wherein the replication-defective recombinant adenovirus lacks at least one region of its genome that is necessary for replication in a target cell.

12. The method of claim 1, wherein the adenovirus is a human Ad 2, a human Ad 5, or a canine CAV-2 adenovirus.

13. A method of treating Parkinson's disease comprising administering into cells of the central nervous system of a mammal suffering therefrom a replication defective recombinant adenovirus comprising ITRs, an encapsidation sequence and a DNA sequence encoding GDNF operably linked to a promoter, wherein the adenovirus E1 gene is non-functional and GDNF is expressed at a level that provides a therapeutic effect.

14. The method of claim 13, wherein the DNA sequence further comprises a secretory sequence in the 5' position and in reading frame with the sequence encoding the GDNF.

15. The method of claim 13, wherein the DNA sequence is a cDNA sequence.

16. The method of claim 13, wherein the DNA sequence encodes human GDNF.

17. The method of claim 13, wherein the DNA sequence encoding GDNF is operably linked to a second sequence enabling expression in nerve cells.

18. The method of claim 13, wherein the promoter is a viral promoter.

19. The method of claim 18, wherein the promoter is an E1A, MLP, CMV, or RSV LTR promoter.

20. The method of claim 13, wherein the DNA sequence is a cDNA sequence encoding human pre-GDNF and the promoter is an RSV LTR promoter.

21. The method of claim 13, wherein the promoter enables expression in nerve cells.

22. The method of claim 21, wherein the promoter is a neuron-specific enolase promoter or a GFAP promoter.

23. The method of claim 13, wherein the replication-defective recombinant adenovirus lacks at least one region of its genome that is necessary for replication in a target cell.

24. The method of claim 13, wherein the adenovirus is a human Ad 2, a human Ad 5, or a canine CAV-2 adenovirus.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:1:

CCGTCGACCT AGGCCACCAT GAAGTTATGG GATGTC    36

```
(2) INFORMATION FOR SEQ ID NO:2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO:2:

CCGTCGACAT GCATGAGCTC AGATACATCC ACACC                                      35
```